United States Patent [19]
Jones

[11] Patent Number: 5,060,641
[45] Date of Patent: Oct. 29, 1991

[54] APPARATUS AND METHOD FOR THE TREATMENT OF FLEXURAL DEFORMITIES, CONTRACTED TENDONS, AND ANGULAR LIMB DEFORMITIES IN FOALS

[75] Inventor: Peyton A. Jones, Monkton, Md.

[73] Assignee: Physicians & Nurses Mfg. Co., Larchmont, N.Y.

[21] Appl. No.: 623,783

[22] Filed: Dec. 7, 1990

[51] Int. Cl.$^5$ .............................................. A61F 5/04
[52] U.S. Cl. .................................... 128/80 R; 128/85; 128/89 R; 128/83; 128/DIG. 20
[58] Field of Search ..................... 128/80 R, 80 B, 82, 128/84 R, 84 A, 87 R, 89 R, 90, DIG. 20, 155, 157, 165, 24 R, 85, 83

[56] References Cited

U.S. PATENT DOCUMENTS

| | | | |
|---|---|---|---|
| 1,019,985 | 3/1912 | McMahon | 128/165 |
| 3,153,413 | 10/1964 | Gottfried | 128/87 R |
| 3,193,984 | 7/1965 | Schubert | 128/DIG. 20 X |
| 3,470,873 | 10/1969 | Walker et al. | 128/89 R X |
| 3,998,219 | 12/1976 | Mercer et al. | 128/90 X |
| 4,033,337 | 7/1977 | Raczkowski | 128/DIG. 20 X |
| 4,300,245 | 11/1981 | Saunders | 128/DIG. 20 X |
| 4,424,809 | 1/1984 | Yovankin | 128/165 |
| 4,922,893 | 5/1990 | Wright et al. | 128/24 R X |

FOREIGN PATENT DOCUMENTS

| | | | |
|---|---|---|---|
| 263203 | 7/1968 | Austria | 128/DIG. 20 |
| 470174 | 5/1969 | Switzerland | 128/DIG. 20 |

Primary Examiner—Richard J. Apley
Assistant Examiner—Linda C. M. Dvorak
Attorney, Agent, or Firm—Paul A. Fattibene; Arthur T. Fattibene

[57] ABSTRACT

A pneumatic cast having an uninflatable longitudinal portion and a circumferential portion to provide support. The pneumatic cast is positioned over the affected leg of a newborn foal to correct various anatomical abnormalities. The pneumatic cast is positioned so that the uninflatable longitudinal portion can provide support for conforming the affected leg to the desired position upon inflation of the pneumatic cast. The uninflatable circumferential portion helps to support and position the pneumatic cast. The pneumatic cast can thereby by inflated to conform the leg without removing weight from the joints which could cause laxity. Anatomical abnormalities such as flexural deformities or contracted tendons and angular limb deformities can be treated.

8 Claims, 2 Drawing Sheets

APPARATUS AND METHOD FOR THE TREATMENT OF FLEXURAL DEFORMITIES, CONTRACTED TENDONS, AND ANGULAR LIMB DEFORMITIES IN FOALS

FIELD OF THE INVENTION

This invention relates generally to the treatment of foals having anatomical abnormalities, and particularly to a pneumatic cast and method of treatment using the pneumatic cast.

BACKGROUND OF THE INVENTION

Neonatal foals often exhibit various abnormalities. One type of abnormality is anatomical abnormalities. Several such abnormalities may be weakness of the pasterns and fetlocks, flexural deformities, or contracted tendons and angular limb deformities. These anatomical abnormalities affect the legs of the newborn foal.

These anatomical abnormalities may be inherited, or may be caused by viral infection, nutritional deficiencies, exposure to the mare of toxins or drugs, or malpositioning of the fetus in-utero. However, the cause of many anatomical abnormalities is still unknown, and mostly speculative at present.

Many of these abnormalities in young foals are treated with corrective splints, braces, or casts. However, these devices are difficult to adjust, are heavy, and often result in sores or skin irritation. Additionally, often the adjacent normal leg is injured due to rubbing or striking the device applied to the leg being treated. In some cases, corrective surgery may be necessary.

Therefore, there is a need for improved treatment of neonatal foals having anatomical abnormalities of the legs that will not result in potential complications as arises from conventional treatment.

SUMMARY OF THE INVENTION

The present invention is directed to a pneumatic cast for correcting anatomical abnormalities to the legs of neonatal foals. An inner and outer plastic tube sealed at both ends forms a cavity which is inflated after placement over the foals affected limb. An uninflatable longitudinal portion provides a surface for supporting forces generated from inflating the pneumatic cast. The pneumatic cast is positioned and inflated to align the leg in the desired direction to correct the anatomical abnormality. An uninflatable portion near the bottom provides additional support.

The cast is positioned, inflated, adjusted, and removed in a method of treatment improving the likelihood of recovery of the affected foal.

Accordingly, it is an object of the present invention to provide improved treatment of foals having contracted tendons, or flexural deformities and specific angular limb deformities.

It is a further object of the present invention to prevent additional injury to foals being treated.

It is a advantage of the present invention that it is light weight.

It is a further advantage of the present invention that it is easily adjusted to optimize treatment.

It is a feature of the present invention that an uninflatable longitudinal portion provides support for the application of forces needed for treatment.

It is a further feature of the present invention that an annular uninflated collar contributes to support and secures placement on the leg of the foal.

These and other objects, advantages and features will become readily apparent in view of the following more detailed description.

DETAILED DESCRIPTION OF THE PREFERRED EMBODIMENT

Figure 1:
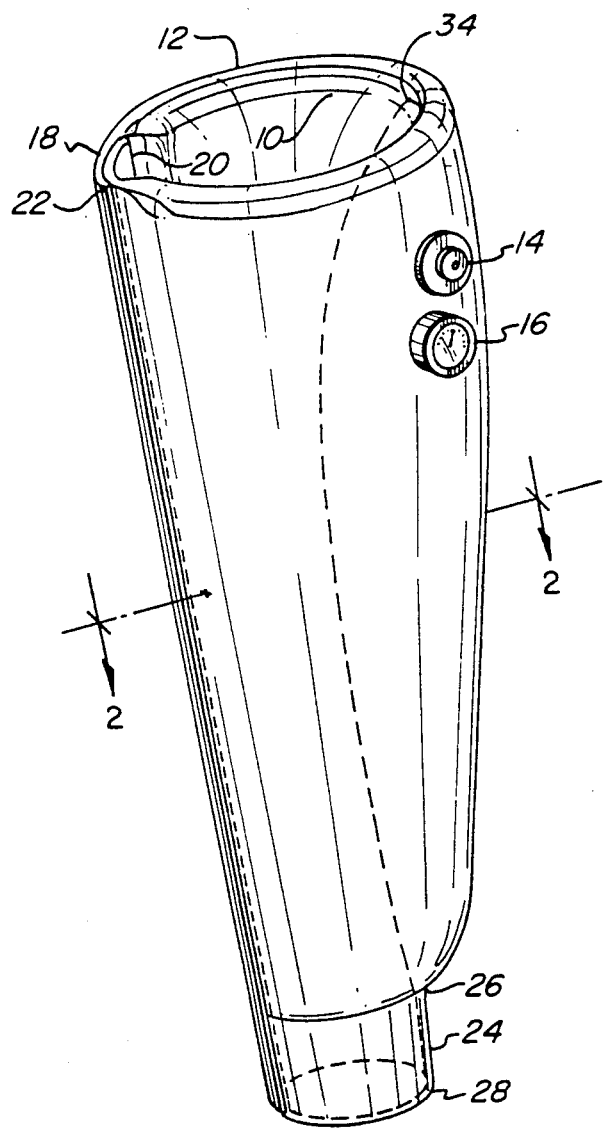
FIG. 1 is a perspective view generally illustrating the present invention.

FIG. 1 illustrates the present invention. The pneumatic cast illustrated in FIG. 1 is formed from a tubular inner wall 10 and an tubular outer wall 12. The inner and outer walls 10 and 12 are sealed at the top by seam 34. The outer wall 12 has a valve 14 therein. Valve 14 is used to inflate the device. Valve 14 can be any valve, such as a tire valve. Gauge 16 is also positioned on outer wall 12. Gauge 16 measures the pressure within the cavity formed between inner wall 10 and outer wall 12 while the pneumatic cast is being inflated. A gauge can also be used on the pump used to inflate the pneumatic cast rather than on the pneumatic cast itself. Along one side of the pneumatic cast is an uninflatable longitudinal portion 18. The uninflatable longitudinal portion 18 is formed by a first longitudinal seam 20 and a second longitudinal seam 22. The seams 20 and 22 extend the entire length of the pneumatic cast. The longitudinal portion 18 has a width of approximately two inches.

At the bottom of the pneumatic cast, there is an uninflatable circumferential portion 24. The uninflatable circumferential portion 24 is formed by a first circumferential seam 26 and a second circumferential seam 28, thereby forming a circumferential portion 24 that remains uninflated.

The inner wall 10 and outer wall 12 can be made of any suitable material such as plastic or urethane. The material can be transparent or opaque. The seams made therein can be either glued or heat-sealed so that an airtight seal is formed.

Figure 2:
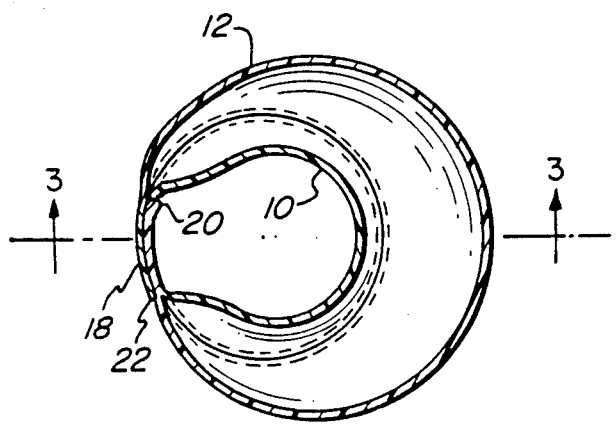
FIG. 2 is a cross section taken along line 2—2 in FIG. 1.

FIG. 2 illustrates more clearly the cavity formed between the inner wall 10 and outer wall 12 when the pneumatic cast is inflated. As can clearly be seen, longitudinal portion 18 remains uninflated.

Figure 3:
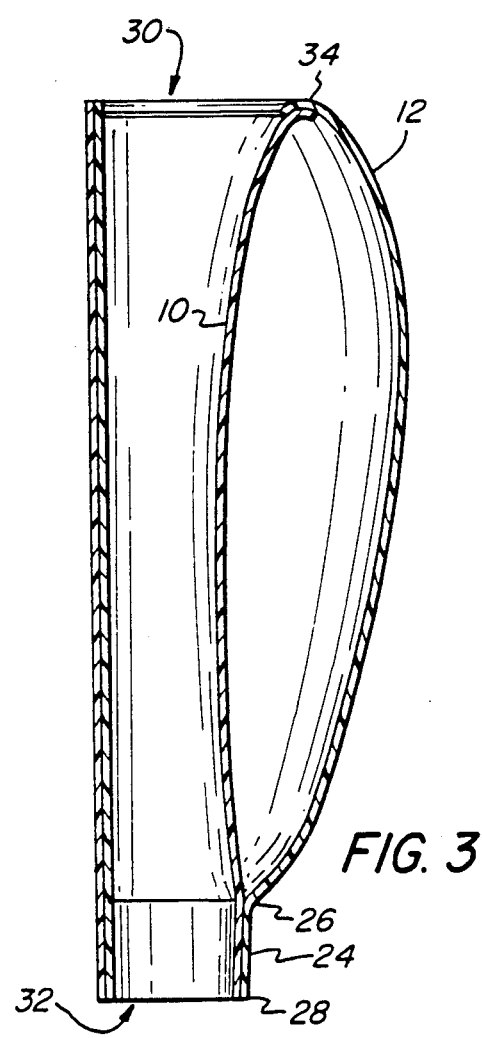
FIG. 3 is a cross section taken along line 3—3 in FIG. 2.

FIG. 3 illustrates the large diameter top opening 30 and the small diameter bottom opening 32. Adjacent the large diameter top opening 30 is top seam 34. Top seam 34 seals the inner wall 10 and outer wall 12.

Figure 4:
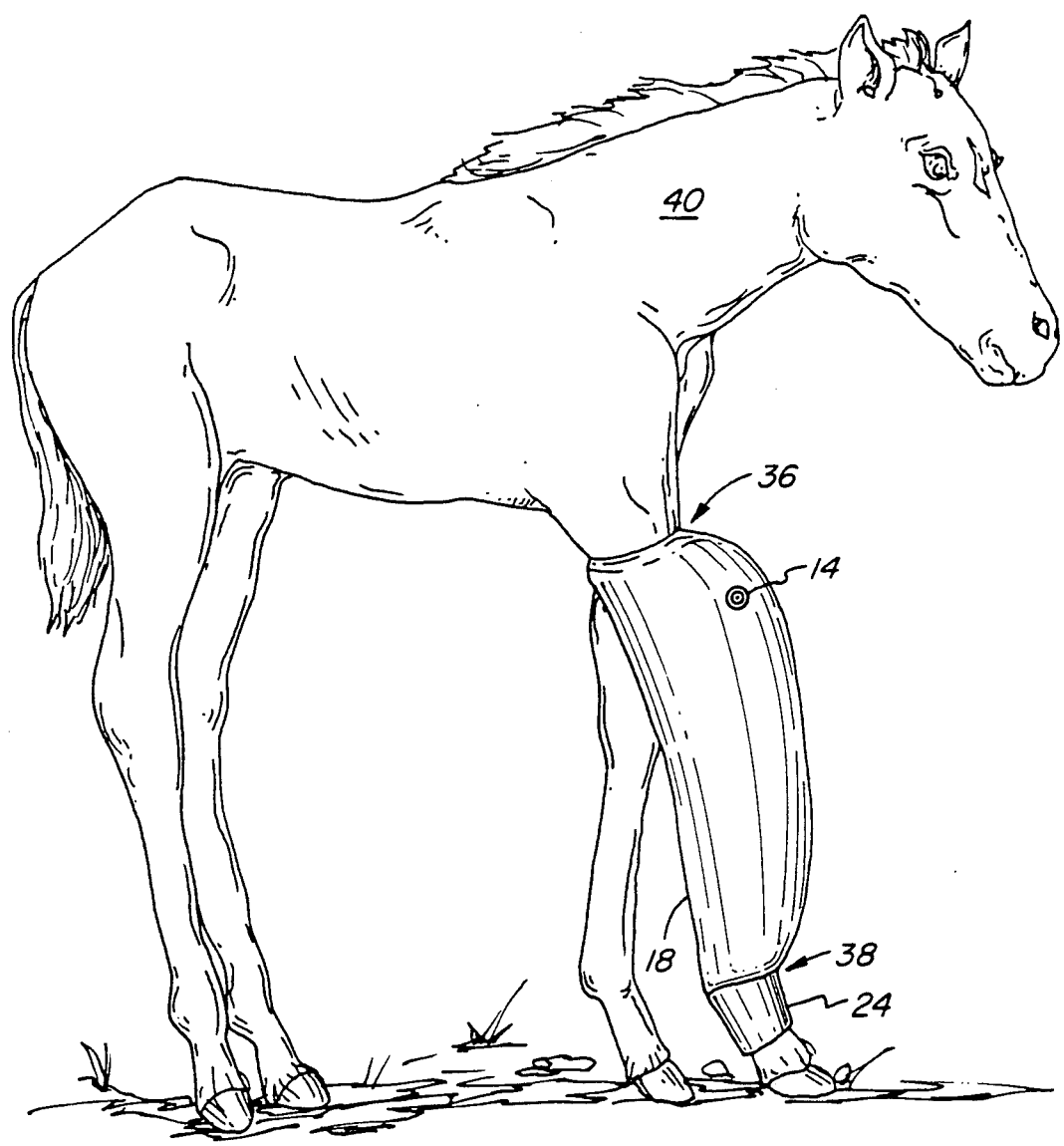
FIG. 4 illustrates the application of the present invention on a foal being treated.

FIG. 4 illustrates the pneumatic cast positioned on a foal having anatomical abnormalities. Abnormalities such as flexural deformities and specific angular limb deformities can be treated.

The pneumatic cast is placed on the affected limb of the foal 40 prior to inflating. The pneumatic cast is positioned s that the top of the inflated section 36 is positioned between the elbow and carpus of the foal 40. The bottom of the inflated section 38 is positioned above the fetlock. The uninflated ircumferential portion 24 therefore extends below the fetlock. The uninflatable longitudinal portion 18 is positioned to rest flat against the leg of the foal 40. Longitudinal portion 18 is also positioned to provide support for the forces generated during inflation to align the affected leg as desired. Once positioned, the pneumatic cast is inflated, using valve 14, forcing the affected leg into the desired conformed position. When properly inflated, the pneumatic cast permits some weight to be placed on the points preventing laxity.

In the treatment of foals, the pneumatic cast will range in length from between twenty and twenty-eight inches. For this range of sizes, the inside diameter of inner wall 10 at the bottom section 38 will be approximately 13.5 inches. The inside diameter at the top section 36 will range from between 17 and 19 inches. The uninflatable circumferential portion 24 has a longitudinal length of approximately 3 inches. The longitudinal portion 18 has a width of approximately 2 inches.

The above described pneumatic cast can be used with various methods of treatment. The preferred method of treatment is to apply a heavily padded support bandage to the affected limb. The support bandage could be dusted with talcum powder and the pneumatic cast placed over the foal's affected leg and the support bandage. The longitudinal portion 18 should be positioned on the foal's affected leg to permit the desired alignment of the affected leg after inflation. The valve stem should be positioned on the lateral or anterior aspect of the leg. This may require a left or right version of the pneumatic cast having the valve stem on the left or right hand side. If needed, tape can be used to secure the circumferential portion 24. The cast can now be inflated with a compressor or pump. The pressure in the pneumatic cast should be adjusted until it results in the desired alignment of the affected leg and allows minimal joint movement when the foal ambulates.

Periods of inflation will depend on the severity of the condition and the age of the foal. Short periods are indicated in newborn foals until their neuromuscular coordination develops and will allow them to stand without assistance. The period of inflation can be increased in ambulatory foals. The patient is observed for any signs of lameness or discomfort and the coronary band is monitored for any changes in temperature or swelling. The support bandage is removed every forty-eight hours and the limb is examined. Changes in conformation are evaluated and the pneumatic cast or splint is reapplied as necessary. The foal should be confined for several days after treatment and may require additional support bandaging. This allows supportive structures of the joints to strengthen and adjust to the altered alignment. Continued exercise restriction is warranted until the limb is anatomically and functionally normal. The above described method has been successful in treating neonatal foals having anatomical abnormalities.

While the pneumatic cast and method of treatment of the present invention has been illustrated and described with respect to the preferred embodiment, it will be obvious to those skilled in the art that various modifications may be made without department from the spirit and scope of this invention.

What is claimed is:

1. A pneumatic cast for the treatment of foals having an anatomical abnormality of the leg comprising:
    a flexible tubular inner wall;
    a flexible tubular outer wall positioned around said inner wall;
    said inner and outer walls having a large diameter opening at one end and a small diameter opening at the other end;
    a top seam sealing the large diameter opening ends of said inner and outer walls together;
    a bottom seam sealing the small diameter opening ends of said inner and outer walls together;
    an intermediate seam extending around a diameter of said inner and outer walls between said top and bottom seams closest to said bottom seam sealing said inner and outer walls together, said intermediate seam placed a substantial distance from said bottom sam wherein the portion between said bottom seams nd said intermediate seam remains uninflated providing support and assisting placement of the pneumatic cast;
    a longitudinal uninflatable portion extending between said top and intermediate seams; and
    a valve placed through said outer wall and entering into the cavity formed between said inner and outer walls between said top seam and said intermediate seam.

2. A pneumatic cast for the treatment of foals as in claim 1 wherein:
    said inner and outer walls are made of plastic.

3. A pneumatic cast for the treatment of foals as in claim 2 wherein:
    said plastic is urethane.

4. A pneumatic cast for the treatment of foals as in claim 2 wherein:
    said longitudinal portion is greater than one inch wide.

5. A pneumatic cast for the treatment of foals as in claim 4 wherein:
    said intermediate seam is at least three inches from the bottom seam.

6. A pneumatic cast for the treatment of foals s in claim 1 further comprising:
    a pressure gauge communicating with the cavity formed between said inner and outer walls between said top seam and said intermediate seam.

7. A pneumatic cast for the treatment of foals having an anatomical abnormality of the leg comprising:
    a double walled inflatable tube having a length between twenty and twenty-eight inches;
    said double walled tube having a large diameter open end, said large diameter open end being of a size sufficient to fit over the top portion of the foal's affected leg, said small diameter open end being of a size sufficient to fit over the bottom portion of the foal's affected leg;
    a circumferential uninflatable portion extending from said small diameter open end between two and four inches toward said large diameter open end;
    a longitudinal uninflatable portion at least one inch wide extending from said large diameter open end to said circumferential uninflatable portion; and
    a valve positioned in said double walled inflatable tube for inflating said double walled inflatable tube, whereby said pneumatic cast can be positioned on the affected leg of the foal and inflated so that the desired alignment of the leg is obtained when the tube is inflated.

8. A method of treating foals having an anatomical abnormality of the leg comprising the steps of:
    applying a padded support bandage to the affected leg;

dusting the padded support bandage with talc powder;

placing a pneumatic tube over the affected leg so that the inflated portion is adjacent the leg surface where pressure is needed;

securing the bottom of the tube to the support bandage;

inflating the tube;

adjusting the pressure in the tube until it results in a desired alignment of the affected leg and allows minimal joint movement when the foal ambulates;

leaving the tube inflated for a period of time;

observing the foal for any signs of lameness or discomfort;

releasing pressure in the tube;

repeating said steps of inflating, adjusting, leaving, observing, and releasing for at least two days;

removing the tube;

examining the foal for any signs of skin irritation or swellings;

continuing said steps of repeating, removing, and examining as necessary;

discontinuing treatment with the tube;

providing support of the affected leg as needed; and limiting the exercise of the foal.

* * * * *